United States Patent
Dreyfuss et al.

[11] Patent Number: 6,011,136
[45] Date of Patent: Jan. 4, 2000

[54] CYCLOPEPTOLIDES

[75] Inventors: Michael Morris Dreyfuss, Basel; Theodor Fehr, Dornach, both of Switzerland; Carolyn Ann Foster, Vienna, Austria; Dieter Geyl, Freiburg, Germany; Berndt Oberhauser, Vienna, Austria

[73] Assignee: Novartis AG, Basel, Switzerland

[21] Appl. No.: 09/068,915

[22] PCT Filed: Nov. 11, 1996

[86] PCT No.: PCT/EP96/05123

§ 371 Date: Jun. 25, 1998

§ 102(e) Date: Jun. 25, 1998

[87] PCT Pub. No.: WO97/19104

PCT Pub. Date: May 29, 1997

[30] Foreign Application Priority Data

Nov. 21, 1995 [GB] United Kingdom ............... 9523744
Mar. 1, 1996 [GB] United Kingdom ............... 9604406
Jul. 4, 1996 [GB] United Kingdom ............... 9613990

[51] Int. Cl.$^7$ .................... A61K 38/08; A61K 38/12; C07K 5/12
[52] U.S. Cl. ................ 530/317; 530/329; 514/11; 514/14
[58] Field of Search ................ 530/317, 329; 514/11, 17

[56] References Cited

U.S. PATENT DOCUMENTS 5,643,869  7/1997  Dreyfuss et al. .................. 514/9
5,686,604  11/1997  Ludescher et al. ................ 540/221

FOREIGN PATENT DOCUMENTS 360 370     4/1995  European Pat. Off. .
7109299     4/1995  Japan .
96/03430 A1 2/1996  WIPO .

OTHER PUBLICATIONS

Foster, C.A., et al., J. of Dermatology, vol. 21, No. 11., pp. 847 to 854, Nov., 1994, "Pharmacological Modulation of Endothelial Cell–associated Adhesion Molecule Expression: Implications for Future Treatment of Dermatological Diseases".

Shionogi & Co., Derwent Abstract 95–196280 [26] (JP 71/9299).

Hommel, U., et al., FEBS Letters, vol. 379, No. 1, pp. 69–73, (1996) "The 3D–structure of a natural inhibitor of cell adhesion molecule expression".

*Primary Examiner*—Michael P. Woodward
*Assistant Examiner*—Anish Gupta
*Attorney, Agent, or Firm*—Gregory D. Ferraro

[57] ABSTRACT

Cyclopeptolides of formula (I), wherein A, B, $R_1$Leu, Leu, C, X and Y are as defined, are inhibitors of adhesion molecule, expression and inhibitors of TNF release and are thus useful for treatment of inflammatory and other diseases which involve increased levels of adhesion molecule expression and/or are mediated by TNF.

(I)

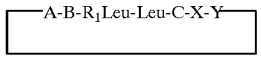

5 Claims, 5 Drawing Sheets

CYCLOPEPTOLIDES

This is a 371 of PCT/EP/96/05123, filed Nov. 20, 1996.

This invention relates to cyclopeptolides and to their therapeutic use as inhibitors of adhesion molecule expression.

Cellular adhesion molecules such as ICAM-1, VCAM-1 and E-selectin are expressed on the surface of endothelial cells, as well as keratinocytes for ICAM-1, in response to pro-inflammatory mediators including TNFα, IFNγ, IL1 and LPS. Corresponding counter-ligands, e.g. LFA-1, VLA4 and SLE$^x$, are expressed on the surfaces of circulating blood cells. Transendothelial migration of leucocytes during inflammatory processes, as well as extravascular cell-cell interactions, are regulated as a result of the interactions between these adhesion molecules and their counter-ligands. Consequently, inhibitors of adhesion molecule expression offer potential for the treatment of many disease states.

Cyclopeptolides are cyclic molecules comprising amino acid residues linked together by peptide bonds and at least one hydroxy substituted carboxylic acid residue which is linked through its hydroxyl substituent to the neighbouring acid residue by an ester linkage.

Our copending patent application, published International patent application WO 96/03430 discloses novel cycloheptapeptolides which are inhibitors of ICAM-1, VCAM-1 and E-selectin expression. We have now discovered further new cycloheptapeptolides of the same general compound class, including compounds having particularly desirable properties.

The present invention provides cycloheptapeptolides of formula I

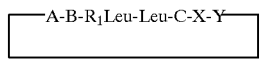

I wherein:
A is a glycolic acid residue optionally α-substituted by
  H, methyl, ethyl, propyl or vinyl, optionally substituted by
    halogen, alkoxy, optionally protected hydroxy or amino, $CSNH_2$, $COOR_2$, vinyl,
    —C≡CH or thiazole,
  wherein $R_2$ is H or lower alkyl,
  optionally substituted by
    alkyl, halogen, cycloalkyl, optionally substituted thiazole, $COOR_2$ or
    —C≡CH,
  wherein $R_2$ is as defined above;
B is an α-amino-γ-methyl-substituted octanoic acid residue;
$R_1$ is hydrogen or methyl;
C is a tryptophan or N-methyl-tryptophan residue of formula II

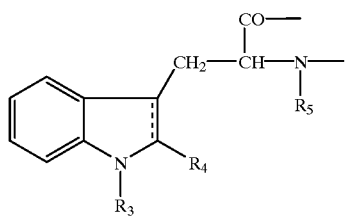

II wherein $R_3$ represents hydrogen, alkoxy, alkyl or benzyl, $R_4$ represents hydrogen or halogen, $R_5$ represents hydrogen or methyl and = represents a single or double bond;
X is an α-amino-substituted ($C_2$ to $C_{14}$) carboxylic acid residue, and
Y is an α-amino- or N-methyl-α-amino substituted ($C_2$ to $C_{10}$) carboxylic acid residue.

In formula I the N-terminal to C-terminal orientation of the amino acid residues is in the clockwise direction, and the peptolide ester bond is between residues A and Y. When $R_1$ is methyl, the residues $R_1$-Leu and Leu are N-methylleucine and leucine residues respectively.

Preferably A is a glycolic acid residue, which is α-substituted by H, methyl, ethyl or propyl optionally substituted by amino, hydroxy, chloro, alkoxy, optionally substituted thiazole, optionally substituted vinyl, cyclopropyl, $CSNH_2$ or —C≡CH.

Preferably C is a N-methyltryptophan residue of formula II, wherein $R_3$ represents hydrogen, ($C_1$ to $C_4$)alkoxy (especially methoxy) or alkyl and $R_4$ represents hydrogen or halogen.

Preferably X is an ox-amino-substituted ($C_4$ to $C_8$) carboxylic acid residue, which is optionally β- or γ-($C_1$ to $C_4$) alkyl substituted. Most preferably X is an α-amino-β- or γ-($C_1$ to $C_4$) alkyl-, especially methyl-, substituted octanoic or a butyric acid residue.

Preferably Y is an N-methyl-α-amino-substituted ($C_2$ to $C_4$) carboxylic acid residue, which is optionally β- or γ-($C_1$ to $C_4$) alkyl-substituted. Most preferably Y is an N-methyl-alanine or N-methyl-valine residue.

The invention includes open chain peptides or peptolides corresponding to the compounds of formula I; for instance, the open chain molecules obtained by either cleavage of the ester bond between residues Y and A or cleavage of an amide linkage between any other adjacent pair of the acid residues. Preferred open-chain derivatives are compounds of formulae IV and V

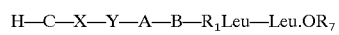   IV and

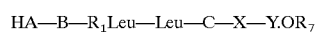   V wherein $R_7$ represents hydrogen or alkyl, e.g. $C_{1-4}$ lower alkyl.

Preferred compounds according to one embodiment of the invention are the compounds of formula Ip

   $I_p$ wherein:
$A_p$ is a glycolic acid residue optionally α-substituted by H, ethyl or methyl;
$B_p$ is an α-amino-γ-methyl-substituted octanoic acid residue;
$R_{1p}$ is hydrogen or methyl;
$C_p$ is a tryptophan or N-methyl-tryptophan residue, which is optionally N'-($C_1$ to $C_4$) alkoxy substituted;
$X_p$ is an α-amino-substituted ($C_2$ to $C_{14}$) carboxylic acid residue, and
$Y_p$ is an α-amino- or N-methyl-α-amino substituted ($C_2$ to $C_{10}$) carboxylic acid residue.

Preferred compounds according to a further embodiment of the invention are compounds of formula $I_p'$

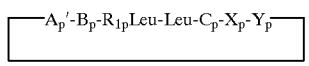

wherein $B_p$, $R_{1p}$, $C_p$, $X_p$ and $Y_p$ are as defined above and $A'p$ is an α hydroxy-substituted butyric acid residue which is γ substituted by a group of formula VI

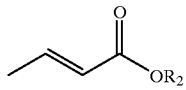

wherein $R_2$ represents a lower alkyl group e.g. a $C_{1-4}$ lower alkyl group.

Most preferably $R_2$ is methyl or ethyl.

Preferred compounds according to a yet further embodiment of the invention are compounds of formula $I_p''$

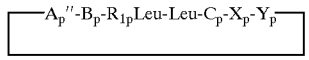

wherein $B_p$, $R_{1p}$, $C_p$, $X_p$ and $Y_p$ are as defined above and $A_p''$ is an a hydroxy substituted butyric acid residue γ substituted by a group of formula VII

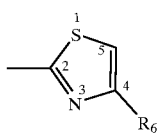

wherein $R_6$ represents hydrogen, lower alkyl or phenyl or forms a carbocyclic ring together with position 5 of the thiazolyl ring.

Compounds of formula I, IV, V, Ip, Ip' and Ip" are hereinafter referred to as "compounds of the invention", which term also includes all the compounds of the invention when in salt or ester form as well as in free form.

The compounds of the invention contain asymmetric atoms and thus may exist in a number of epimeric forms. All of the possible epimers as well as diastereoisomeric mixtures thereof are encompassed in the invention. Epimers which possess inhibition of adhesion molecule expression activity are preferred. In general, e.g. for pharmaceutical use in accordance with the invention, epimers which possess inhibition of adhesion molecule expression activity in pure or substantially pure form (i.e. free or substantially free of epimers which lack inhibition of adhesion molecule expression activity), e.g. comprising at least 90%, e.g. at least 95% of active epimer (i.e. comprising less than 10%, e.g. less than 5% of inactive epimer) will be preferred. Most preferably compounds of the invention have the same cyclopeptolide ring stereochemical conformation as the particularly preferred compound of formula VII below.

Particularly preferred compounds of the invention are the compounds of formulae VIII, IX and X

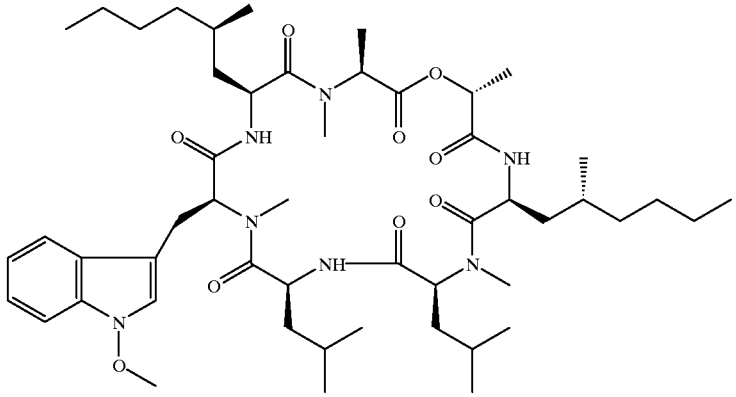

-continued

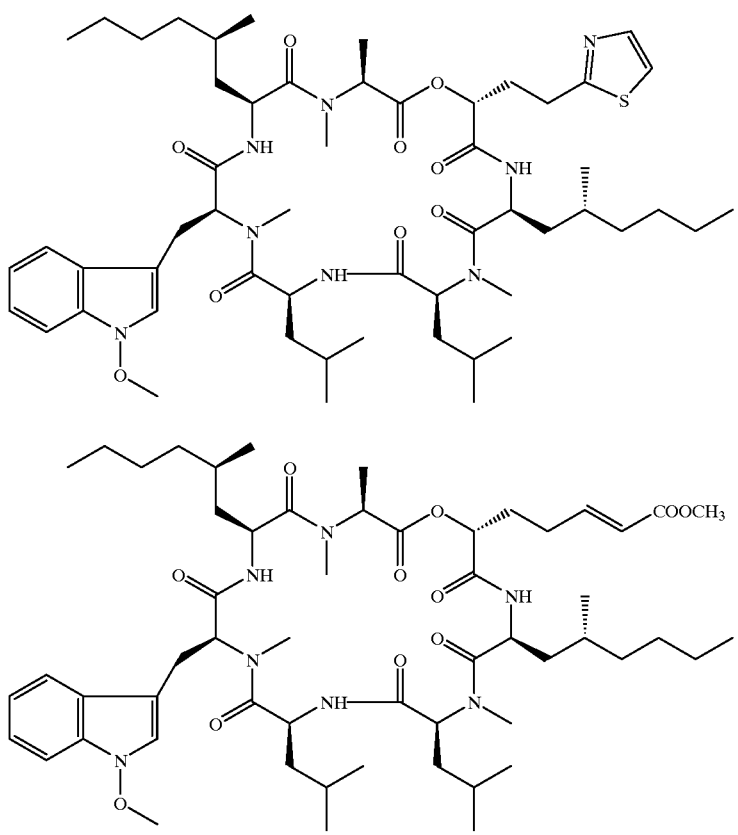

The compound of formula VIII has been isolated from cultures of fungal strain F/94-499709, samples of which were deposited with the DSM-Deutsche Sammlung von Mikroorganismen und Zellkulturen under the provisions of the Budapest Treaty on Sep. 18, 1995 and are identified as deposit number DSM 10275. The characteristics of fungal strain F/94-499709 are described hereinafter in Example 1. The compound of formula VIII is a particular compound of the invention.

Samples of strain F/94-499709 may also be obtained from Sandoz Ltd. CH-4002 Basel Switzerland.

Notice is hereby given that access to samples of DSM 10275 is limited in accordance with the provisions of Rule 28 (4) and (5) EPC.

The invention includes the strain F/94-499709 (DSM 10275) in isolated form and mutants and derivatives thereof as well as all novel cyclopeptolides which are produced by this strain.

The compound of formula VII and related compounds may be obtained by cultivating F/94-499709 (DSM 10275) or a mutant or derivative thereof or similar fungal species in nutrient medium and recovering the compounds therefrom, for example as described in Example 2.

The characteristics of the compound of formula VIII are given in Example 3.

Compounds according to the invention may be prepared by derivatisation of the compounds of formulae XI or XII (as hereinafter described) or VIII, which comprises a) for the preparation of compounds of formula I, wherein A is substituted by $COOR_2$, reacting corresponding compounds of formula I, wherein A is substituted by CN, with nucleophiles, preferably an alcohol, with appropriate basic or acidic catalysis, preferably hydrochloric acid, in organic solvents, preferably ether, or b) for the preparation of compounds of formula I, wherein A is alkoxymethyl substituted, reacting corresponding compounds of formula I, wherein A is substituted by $CH_2$—OH, with alkylating compounds, such as alkylhalogenides or diazo-compounds with or without catalysts, or c) for the preparation of compounds of formula I, wherein A is substituted by $COOR_2$, esterifying corresponding compounds of formula I, wherein A is substituted bag COOH, by standard methods, preferably by conversion into the acid chloride with e.g. thionyl chloride and treatment with an appropriate alcohol in the presence or absence of an acid binder, or d) for the preparation of compounds of formula I, wherein A is substituted by $CH_2OH$, reducing corresponding compounds of formula I, wherein A is substituted by $COOR_2$, with metal hydrides or boron hydrides, preferably borane dimethylsulfide complex, in organic solvents, or e) for the preparation of compounds of formula I, wherein A is substituted by optionally substituted vinyl, reacting corresponding compounds of formula I, wherein A is substituted by CHO, with a Wittig reagent, or f) for the preparation of compounds of formula I, wherein A is substituted by $CH_2NH_2$, reducing corresponding compounds of formula I, wherein A is substituted by $CH_2N_3$, or g) for the preparation of compounds of formula I, wherein A is substituted by C≡CH, dehydrogenating corresponding compounds of formula I, wherein A is substituted by CH=CBr$_2$, or h) for the preparation of compounds of formula I, wherein A is substituted by cyclopropyl, reacting corresponding compounds of formula I, wherein A is substituted by vinyl, with diazomethane, or i) for the preparation of compounds of formula I, wherein A is substituted by CSNH$_2$, reacting corresponding compounds of formula I wherein A is substituted by CN with sulfur derivatives, preferably with diphenylphosphinodithioic acid, e.g. by refluxing a solution of the sulphur compound with a compound of formula I wherein A is substituted by CN, or j) for the preparation of preferred compounds of formula $I_p''$

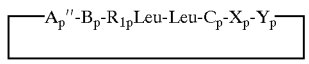   $I_p''$ wherein the substituents are as defined above, reacting a compound of formula $I_p''$ wherein $A_p''$ represents an a-hydroxy-substituted butyric acid residue γ-substituted by —CS—NH$_2$, with a α-halogencarbonyl compound of formula XIII

   XIII wherein R$_6$ is as defined above and Hal represents halogen, or with the acetal of the compound of formula XIII
(The reaction may be carried out according to known methods, e.g. reacting a solution of a compound of formula II in a solvent inert under reaction conditions, e.g. in dimethylformamide or pyridine, at elevated temperature, preferably at 60° to 100° C. The end products may be isolated and purified by conventional techniques.), or k) for the preparation of preferred compounds of formula $I_p'$

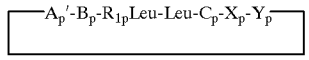   $I_p'$ wherein the substituents are as defined above, reacting a compound of formula Ip' wherein $A_p'$ represents an a-hydroxy-substituted butyric acid residue which is y-substituted by —CHO, with alkoxycarbonylmethylenetriphenylphosphorane and isolating the compounds of formula $I_p'$, or l) for the preparation of compounds of formula I, wherein R$_3$ represents hydrogen, removing the methoxy group from compounds of formula I, wherein R$_3$ represents OCH$_3$, or m) for the preparation of compounds of formula I, wherein the symbol = represents a single bond, reducing compounds of formula I, wherein the symbol = represents a double bond, or n) for the preparation of compounds of formula L wherein R$_3$ represents alkyl or benzyl, introducing these groups into compounds of formula I, wherein R$_3$ represents hydrogen, or o) for the preparation of compounds of formula I, wherein R$_4$ represents halogen, halogenating compounds of formula I, wherein R$_4$ represents hydrogen, or p) for the preparation of compounds of formula I, wherein R$_3$ represents alkoxy and the symbol = represents a double bond, reacting compounds of formula I, wherein R$_3$ represents hydrogen and the symbol = represents a single bond, with an alkali tungstate and hydrogen peroxide and alkylating the N-hydroxy-indol-intermediate, and if desired isolating the compound of formula I.

In preferred embodiments of a) to i) above the compounds of formula I are compounds wherein A is an α-hydroxy butyric acid residue which is γ-substituted by COOR$_2$, CN, alkoxymethyl, CH$_2$—OH, COOH, optionally substituted vinyl, CHO, CH$_2$NH$_2$, CH$_2$N$_3$, C≡CH, CH=CBr$_2$, cyclopropyl or vinyl as appropriate.

Intermediates for preparation of compounds of formula I may be prepared as follows:

(i) for preparation of intermediates wherein A is substituted by —CHO, oxidising corresponding compounds of formula I wherein A is substituted by —CH$_2$OH, and (ii) for preparation of intermediates wherein A is substituted by —COOH, hydrolysing corresponding compounds of formula I wherein A is substituted by COOAlkyl, with mineral acid e.g. HCl in aqueous alcoholic solution, or with base.

Intermediates, for preparation of compounds of formula I, wherein A is substituted by —CN include natural compounds. For example compounds of formula XI and XII.

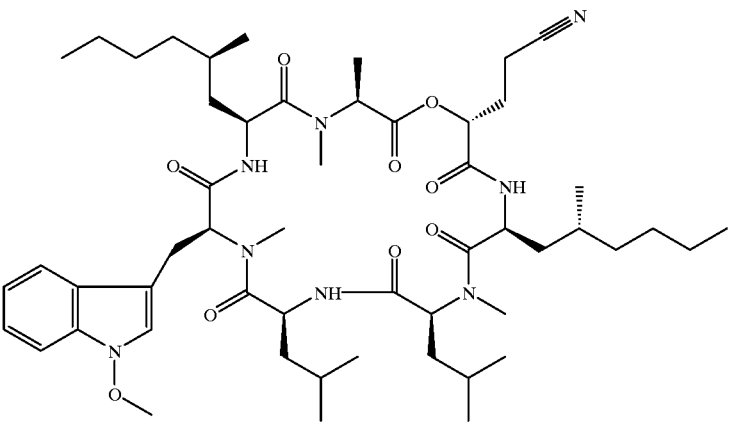

XI

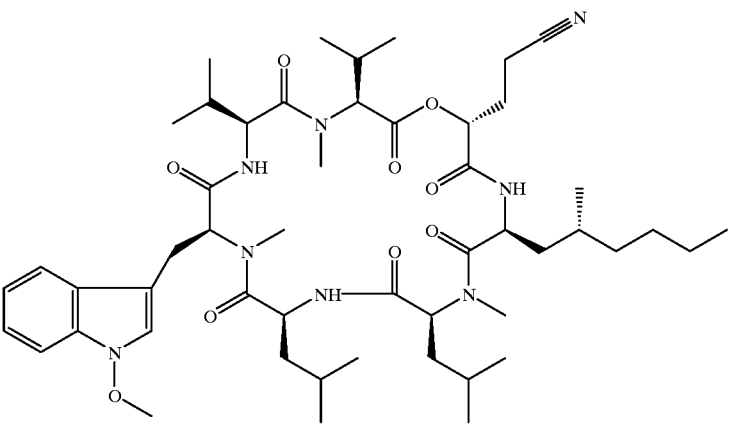

XII are obtainable as isolates from cultures of fungal strain F92-4471/08, deposited with the US Department of Agriculture, NRRL culture collection under the provisions of the Budapest Treaty on Jul. 2, 1993 and identified as deposit number NRRL 21123. The characteristics of fungal strain F92-4471/08 and the isolation of compounds XI and XII are described in detail in our copending patent application, International patent application WO 96/03430.

The compounds of the invention may be prepared also by chemical synthesis; for example, using conventional peptide synthesis techniques. Typically the final step in the preparation of the compounds is a cyclisation step in which a linear peptide or peptolide comprising the acid residues A, B, $R_1$Leu, Leu, C, X and Y linked together in appropriate order is cyclised by an amide- or ester-bond forming reaction.

Thus the invention includes a process for the preparation of a cyclic peptolide of formula I comprising cyclisation of a linear peptide or peptolide comprising the acid residues A, B, $R_1$Leu, Leu, C, X and Y linked together in appropriate order.

The compounds of the invention exhibit pharmacological activity and are therefore useful as pharmaceuticals. In particular the compounds of the invention are inhibitors of the stimulated expression of cellular adhesion molecules, especially inhibitors of VCAM-1 relative to E-selectin and ICAM-1 expression. In particular also the compounds of the invention are inhibitors of the release of TNF, e.g. inhibitors of the release of TNFα.

Assays which may be used to detect the inhibition of ICAM-1, VCAM-1 and E-selectin expression and the inhibition of TNFα release by the compounds of the invention are described after the Examples.

Thus, in view of their activity as inhibitors of cellular adhesion molecule expression, the compounds are useful for the treatment or prophylaxis of disease processes which involve expression of cellular adhesion molecules. These disease processes include many acquired and inherited diseases/disorders where leucocyte activation and trafficking play a prominent role in the pathogenic process, most notably acute and chronic inflammation (e.g. allergy, asthma, dermatitis, psoriasis, reperfusion injury and septic shock), autoimmune states (e.g. diabetes, multiple sclerosis and rheumatoid arthritis) and immune-mediated neurodegeneration (e.g. acquired immunodeficiency disorders). Other indications for the compounds of the invention include tumour metastasis (e.g. melanoma, osteocarcinoma), atherosclerosis and allograft/xenograft rejection, since it is known that inhibition of vascular adhesion molecules can greatly improve the prognosis of these processes.

Also the compounds of the invention have therapeutic potential in hyperproliferative skin diseases (e.g. psoriasis) as well as various malignancies in view of their inhibitory activity at submicromolar concentrations when tested for 72 hours in a keratinocyte-based as well as other proliferation assays.

The compounds of the invention are active in inhibiting TNFα/IL-6-induced HIV production in the U1 monocytic cell line, as evaluated by p 24 ELISA and are therefore useful in the treatment of immunodeficiencies and virally caused diseases, especially in the treatment of AIDS.

Furthermore, in view of their activity as inhibitors of TNF release, the compounds of the invention are useful for the prophylaxis or treatment of diseases or pathological conditions mediated by TNF, especially TNFα, e.g., inflammatory conditions, autoimmune diseases, severe infections, and organ or tissue transplant rejection including both allograft and xenograft rejection, e.g. for the treatment of recipients of heart, lung, combined heart-lung, liver, kidney, pancreatic, skin or corneal transplants and for the prevention of graft-versus-host disease, such as following bone marrow transplants.

The compounds of the invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which the compounds of the invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idio-pathic sprue, autoimmune inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

The compounds of the invention are also useful for the treatment, prevention, or amelioration of asthma, bronchitis, pneumoconiosis, pulmonary emphysema, and other obstructive or inflammatory diseases of the airways.

The compounds of the invention are useful for treating undesirable acute and hyperacute inflammatory reactions which are mediated by TNF, especially by TNFα, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Thus the invention also includes the therapeutic use of, and therapeutic compositions containing, the compounds of the invention.

In particular the invention includes methods for the treatment or prophylaxis of diseases which involve expression of adhesion molecules which comprise administering a therapeutically or prophylactically effective amount of a compound according to the invention to a subject.

The invention also includes therapeutic compositions comprising a therapeutically effective amount of a compound according to the invention.

Furthermore the invention includes the use of a compound according to the invention for the preparation of a medicament for application in the treatment or prophylaxis of diseases which involve expression of adhesion molecules.

In particular the invention also provides in a further series of embodiments:

A. A method of inhibiting production of soluble TNF, especially TNFα, or of reducing inflammation in a subject (i.e., a mammal, especially a human) in need of such treatment which method comprises administering to said subject an effective amount of a compound of the invention, or a method of treating any of the above mentioned conditions, particularly a method of treating an inflammatory or autoimmune disease or condition, e.g., multiple sclerosis or rheumatoid arthritis, or alleviating one or more symptoms of any of the above mentioned conditions.

B. A compound of the invention for use as a pharmaceutical, e.g. for use in the prophylaxis or treatment of diseases or pathological conditions mediated by TNF, e.g. as an immunosuppressant or antiinflammatory agent or for use in the prevention, amelioration or treatment of any disease or condition as described above, e.g., an autoimmune or inflammatory disease or condition.

C. A pharmaceutical composition comprising a compound of the invention in association with a pharmaceutically acceptable diluent or carrier, e.g., for use in the prophylaxis or treatment of diseases or pathological conditions mediated by TNF, e.g. as an immunosuppressant or anti-inflammatory agent or for use in the prevention, amelioration or treatment of any disease or condition as described above, e.g., an autoimmune or inflammatory disease or condition.

D. Use of a compound of the invention in the manufacture of a medicament for use in the prophylaxis or treatment of diseases or pathological conditions mediated by TNF, e.g. as an immunosuppressant or anti-inflammatory agent or for use in the prevention, amelioration or treatment of any disease or condition as described above, e.g., an autoimmune of inflammatory disease or condition.

The compositions may be for parenteral, oral, aerosol, inhalation or topical use and usually comprise one or more pharmaceutically acceptable carriers diluents or excipients and may comprise additives such as stabilisers and the like.

The dosages of the compounds used may be varied having regard to the condition or disease involved, whether the use is for treatment or prophylaxis thereof and the mode and route of administration among other things. In general, however satisfactory results are obtained on administration orally at dosages of from about 0.05 to about 10 mg/kg/day, preferably from about 0.1 to about 7.5 mg/kg/day, more preferably from about 0.1 to about 2 mg/kg/day administered once or, in divided doses, 2 to 4 times per day. Alternatively for parenteral administration, e.g. by iv drip or infusion, dosages from about 0.01 to about 5 mg/kg/day, preferably from about 0.05 to about 1 mg/kg/day and more preferably from about 0.1 to about 1.0 mg/kg/day may be used. Suitable daily dosages for human patients are thus from about 2.5 to about 500 mg p.o., preferably from about 5 to about 250 mg p.o., more preferably from about 5 to about 100 mg p.o.; or from about 0.5 to about 250 mg i.v., preferably from about 2.5 to about 125 mg i.v. and more preferably from about 2.5 to about 50 mg i.v.

The compounds may be administered by any appropriate route, including enterally, parenterally and topically or by inhaler. Suitable enterally administered forms ire solutions for drinking, tablets or capsules. Suitable parenteral forms are injectable solutions or suspensions. Suitable forms for topical administration include creams, lotions and the like at a concentration range of 0.01–10%, preferably from 0.1 to 1%, by weight for such formulations. Suitable unit dosage forms for oral administration may comprise from 1 to 50 mg of the compound, usually from 1 to 10 mg.

The invention is further described, by way of illustration only, in the following examples which refer to the accompanying diagrams in which.

EXAMPLES

Example 1

Characterization of strain F/94-499709 (DSM 10275)

Figure 1:
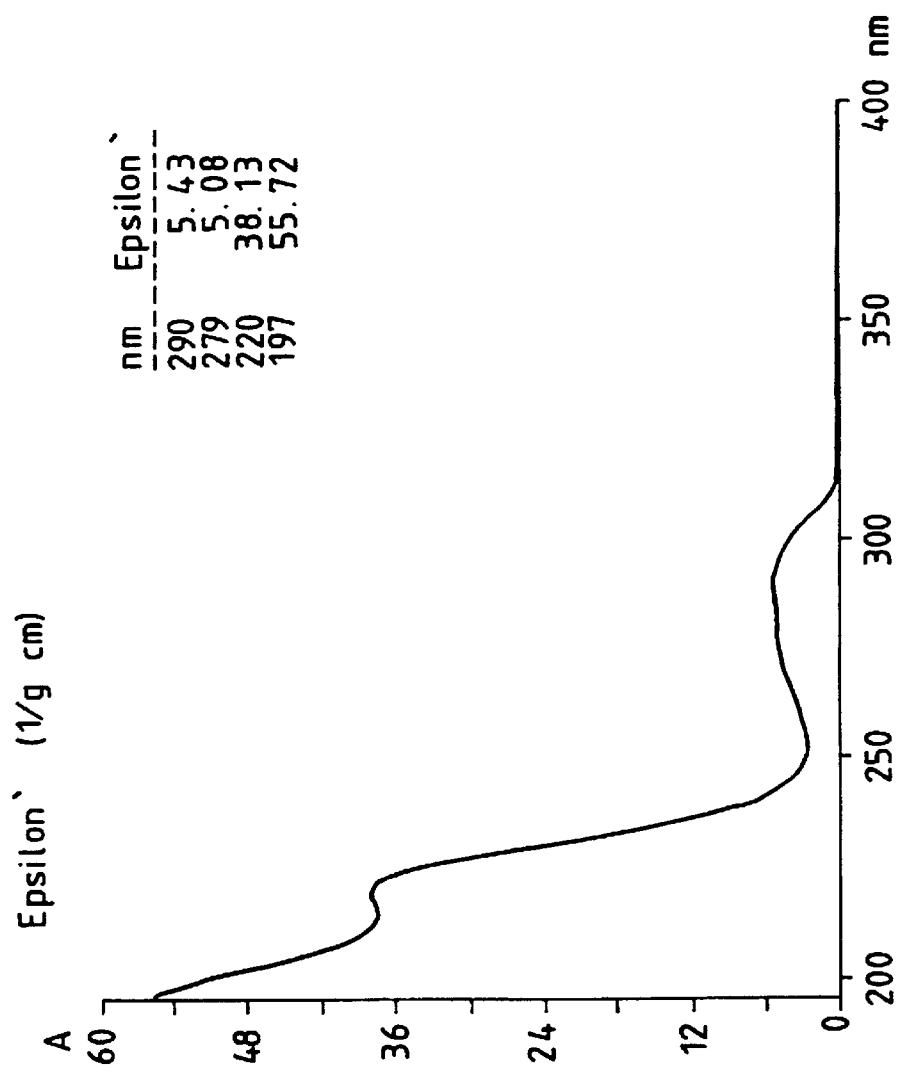
FIG. 1 shows the UV spectra of the compound of formula VIII.

The following medium is used to characterise the strain F/94-499709, in which the media components are given as weight/volume in de-ionized water and heat sterilization is performed for 20 minutes at 121° C.

MEA: 2% malt extract, 0.4% yeast extract, 2% agar.

The strain F/94-499709 shows the following characteristics when point-inoculated on MEA in Petri dishes and incubated in the dark:

The optimal temperature for growth is between 24 and 30° C. After 14 days of incubation colonies attain a diameter of 25 to 32 mm at 24° C., 30 to 37 mm at 27° C. and 7 to 15 mm at 33° C. Above 37° C. and below 13° C. strain F/94-499709 does not show any growth.

Colonies growing at 27° C. in the dark are generally cream colored to light buff, remain rather flat to slightly raised, with little and restricted whitish to light gray aerial mycelium developing in the center. Radial furrows can become conspicuous, and when viewed from the bottom, darker gray concentric zones can become predominant. In aging cultures the aerial and substrate mycelium in the central parts of the colonies can become dark gray, whereas the colony edges remain cream colored to light buff.

Upon microscopic examination no sporulating structures have been observed and thus strain F/94-499709 is tentatively termed a mycelium sterilum.

Example 2

Fermentation of strain F/94-499709.

The following media and procedures are suitable for use in a process of producing the compound of formula VIII by fermentation of the strain F/94-499709. If not otherwise stated, all media components are given as weight/volume in de-ionized water and heat sterilization is performed for 20 minutes at 121° C.

PCM (pre-culture and intermediate culture medium): 2% malt extract, 0.4% yeast extract, 0.1% agar.

PRM (production medium): 2% soluble starch, 0,5% yeast extract, 2% glucose, 2% corn steep liquor, 0,5% peptone, 0,2% calcium carbonate.

Pre-cultures are produced by thawing two ml of a liquid nitrogen seeding suspension of strain F/94-499709, inoculating them into a 500 ml-Erlenmeyer flask containing 200 ml PCM, and incubating it at 24° C. for seven days on a rotary shaker at 200 RPM.

For the production of the primary intermediate culture fourteen 500 ml-Erlenmeyer flasks each containing 200 ml PCM are inoculated each with five ml of the pre-culture.

Secondary intermediate cultures are produced by inoculating two 50 Liter fermentors containing PCM each with 1.4 Liters of primary intermediate cultures. The fermentation was carried out for six days under the following conditions: 24° C., 1 Liter air/minute/Liter medium, blade stirrers rotating at 150 RPM and 0.5 bar pressure. For the production of the compound of formula VIII and related compounds 13 Liters of the secondary intermediate culture were inoculated into each of three 500 Liter fermentors containing PRM. The fermentation was carried out under the following conditions: 21° C., 1 Liter air/minute/Liter medium, blade stirrers rotating first at 100 RMP and gradually increasing to 150 RPM and 0.5 bar pressure. 1500 Liters of the production fermentation were harvested and combined after 96 hours for recovery of desired compound of formula VIII and related compounds.

Example 3

Isolation of the peptolide of formula VIII from the strain F/94-499709.

The broth from the 1500 liters fermentation together with 1700 liters of ethyl acetate is homogenised in a Dispax reactor and stirred vigorously for 3 hours. The organic phase is separated with the aid of a Westfalia separator. This extraction step is repeated and the organic phases evaporated together under reduced pressure to give 2745 g of extract. The extract is defatted by a three step extraction with 40 liters of methanol/water mixture (9:1) and 40 liters of cyclohexane. The methanol fractions are combined and evaporated to dryness under reduced pressure to yield 960 g of defatted extract. This extract is chromatographed on a column of 15 kg of Sephadex LH20 in methanol solution to give fractions totalling 135 g containing the peptolide of formula VIII. 300 g of Silicagel are impregnated with this 135 g fraction total and the impregnated Silicagel is then added on to the top of a column of 1.5 kg of Silicagel Merck 0.04 to 0.063 mm and chromatographed with 1 liter methyl-tertiarybutylether/cyclohexane 1:9, 2:8, 3:7, 4:6, 5:5, 6:4, 7:3, 8:2, 9:1, 3 liters MTBE and 3 liters of MTE/methanol 95:5.

Fractions of 1 liter are collected and analysed by HPLC and TLC. Fractions 8 and 9 are combined and evaporated to dryness. Crystallisation from ether yields 21.9 g of pure peptolide of formula VIII. Further purification of the mother liquor and fractions 10 to 13 by chromatography on Silicagel H Merck (750 g) in a similar way as described above yields a further batch of crystalline cyclopeptolide of formula VIII. The peptolide is found to have a melting point (mp) of 143–146° C. when purified from ether and an optical rotation $[\alpha]_D^{20}$=–233.9°(c=0.908, Methanol). The peptolide of formula VIII, has an IC$_{50}$ of about 2 nM when tested in the VCAM-1 cell ELISA.

Figure 2:
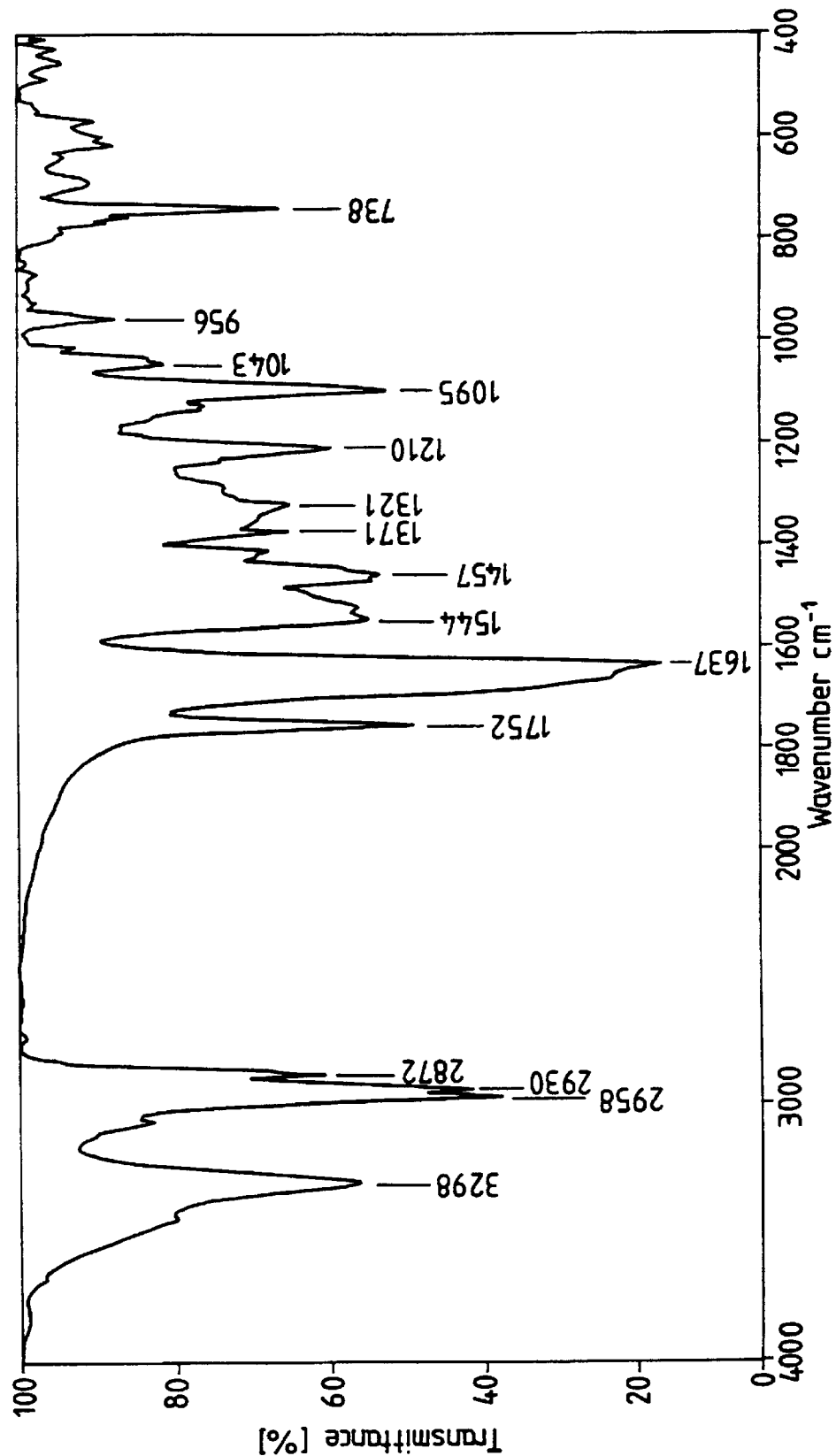
FIG. 2 shows the IR spectrum of the compound of formula VIII.
Figure 3:
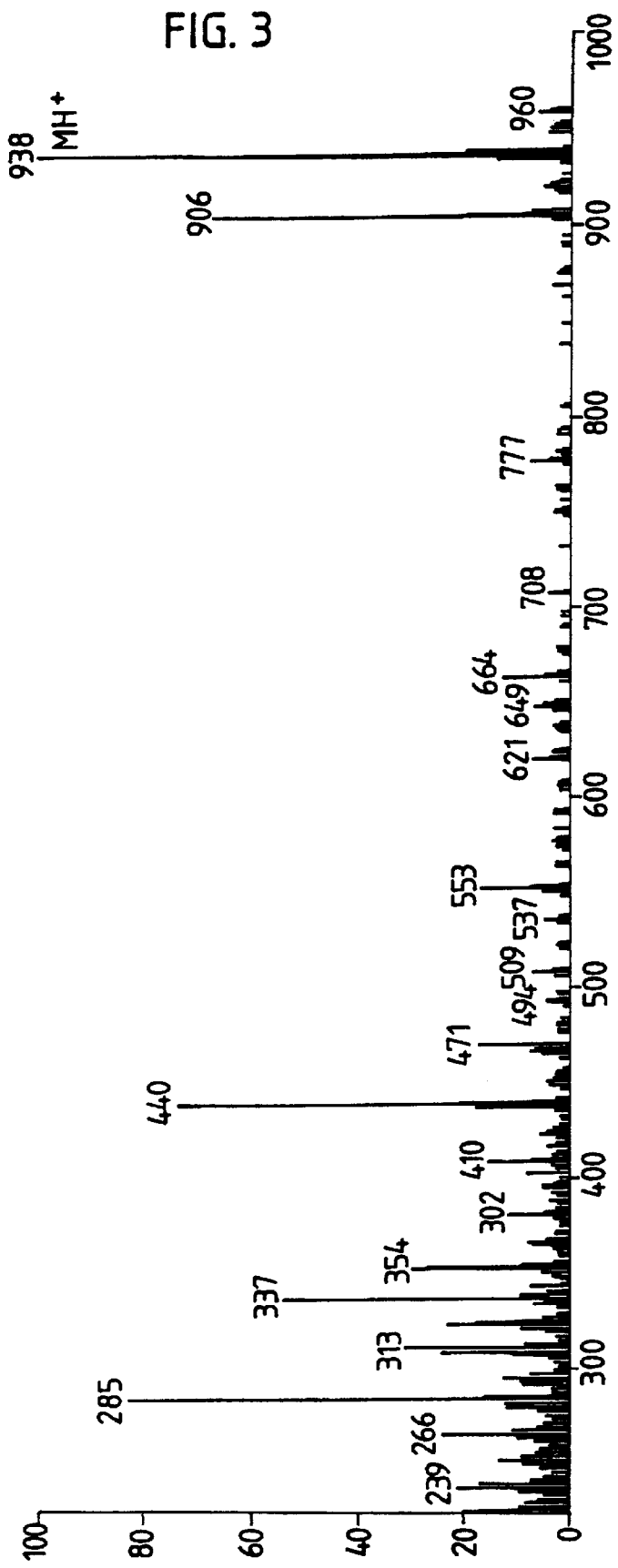
FIG. 3 shows the FD-Mass spectrum of the compound of formula VIII.
Figure 4:
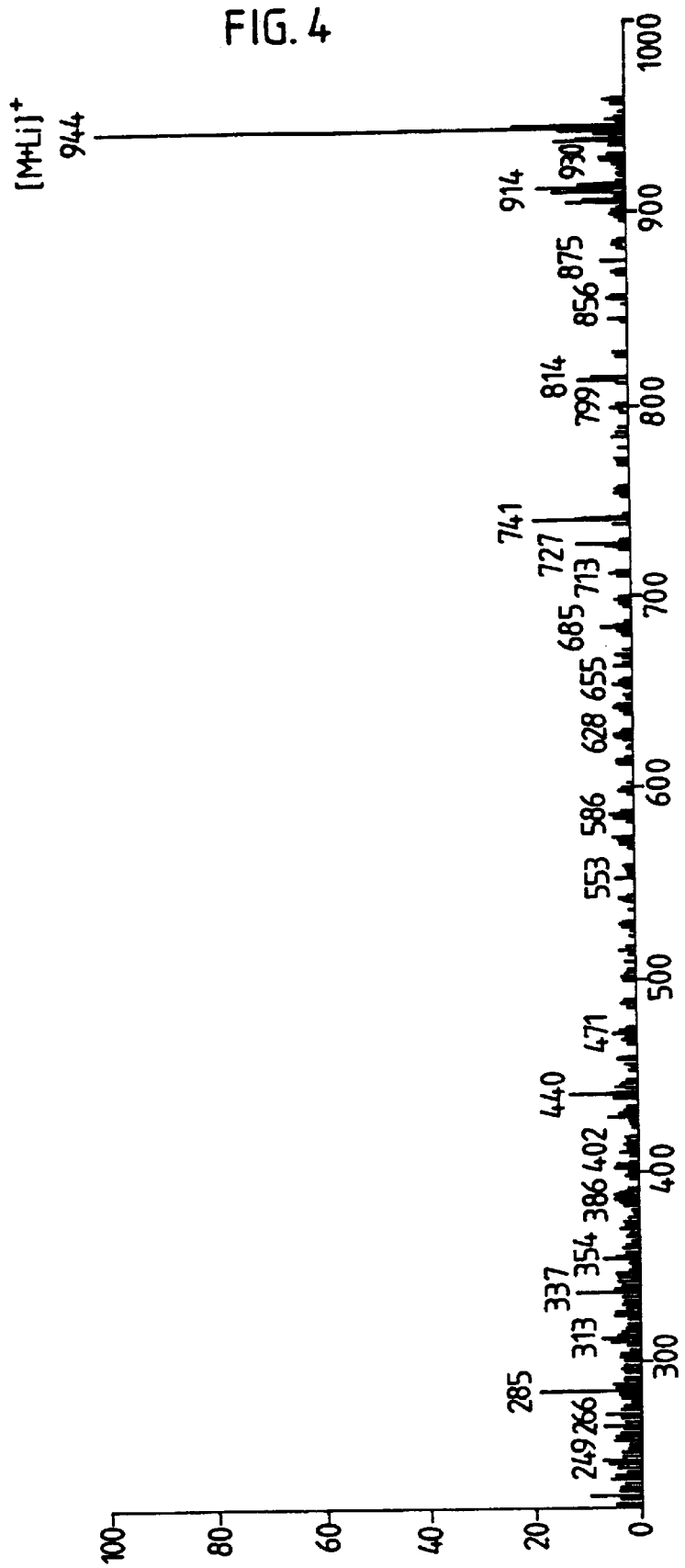
FIG. 4 shows the FD-Mass spectrum (with addition of LiI) of the compound of formula VIII.
Figure 5:
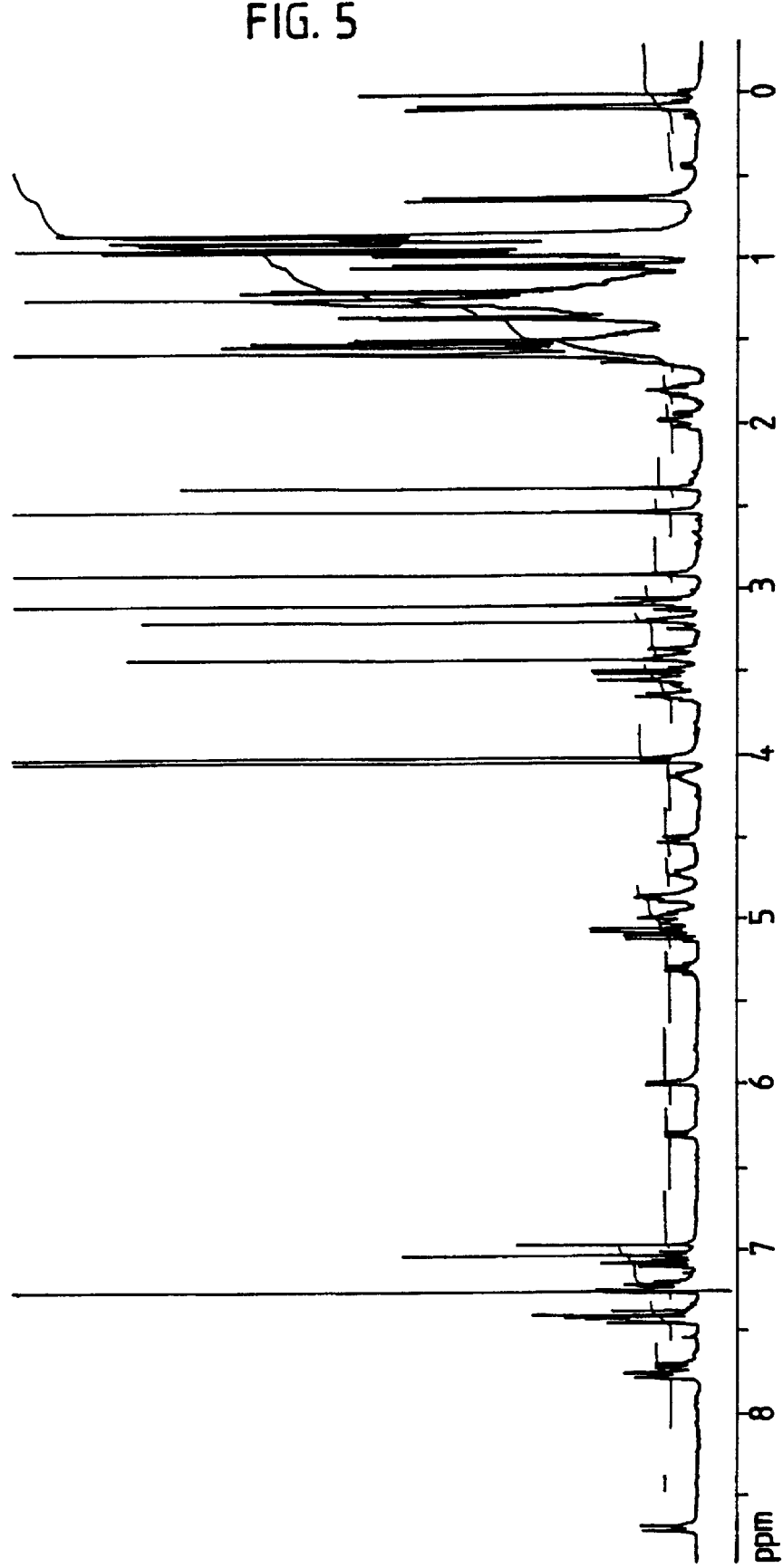
FIG. 5 shows the proton NMR spectrum of the compound of figure VIII in CDCl$_3$.

Molecular formula: C$_{51}$H$_{83}$N$_7$O$_9$ (938.3) UV-Spectrum in methanol: γmax (ε')=290 (5.4), 279 (5.08), 220 (38.1), 197 (55.7).—see FIG. 1 IR (KBr) spectrum given in FIG. 2 MS FAB spectrum given in FIG. 3 MS FAB spectrum (with LiI) given in FIG. 4 proton NMR spectrum in CDCl$_3$ given in FIG. 5 MTBE=methyl tertiary butyl ether VCAM=vascular adhesion molecule

Example 4

Synthesis of the N1'-Desmethoxy derivative of the the compound of formula VIII

A solution of 4.9 mg of the compound of formula VIII is dissolved in 3 ml methanol and 8 mg of palladium on charcoal (10%) is added. The mixture is stirred under an atmosphere of hydrogen for 2 hours, flushed with argon, filtered and evaporated to yield the title compound as colourless foam. The compound is analysed by thin layer chromatography and NMR spectroscopy and the following results are obtained.

TLC: silica gel, toluene/methanol 9/1, Rf=0.28. 1H-NMR (3 conformers 56:37:7, marked with *°', characteristic signals given): 8.72* (d, J=10 Hz, NH); 8.08* (s, br, indole NH); 6.97*, 6.90° (2d, J=2 Hz, indole H-2); 6.34° (d, J=9.5 Hz, NH); 6.00* (d, J=6.5 Hz, NH); 5.83' (d, NH); 5.32° (ddd, PrLeu alpha-H); 5.12°, 5.08* (2q, J=7 Hz, lactic acid Me); 4.50* (dd, MeLeu alpha-H); 4.10* (ddd, Leu alpha-H); 3.42 (q, J=7 Hz, MeAla alpha-H); 3.43°, 3.19°, 3.12*, 2.93*, 2.53*, 2.35° (6s, NMe); 1.54*, 1.5°° (2d, J=7 Hz, MeAla alpha-H), 1.38°, 1.24* (2d, J=7 Hz, lactic acid alpha-H); 0.57*, −0.01* (2d, J=6.5 Hz, Me), −0.19* (ddd, Leu beta-H).

Example 5

Synthesis of the N1'-Methyl derivative of the compound of formula VIII

A solution of 5 mg of the product of example 4 in 0.5 ml dry DMF is mixed with 100 ml iodomethane and a solution of 3 mg of sodium bis(trimethylsilyl)amide in 0.3 ml DMF is added. After stirring of the reaction mixture for 1.5 h at RT, the mixture is poured onto 0.1 M aqueous HCl, extracted with ethyl acetate and partitioned between ethyl acetate and saturated aqueous bicarbonate solution. The organic phase is washed with brine, dried over sodium sulfate and evaporated in vacuo. The crude product is purified by chromatography on silica gel (gradient: toluene/methanol=100/0.25 to 100/2.5) to yield the title compound as a colorless foam. The compound is analysed by thin layer chromatography and NMR spectroscopy and the following results are obtained.

TLC: silica gel, toluene/methanol 9/1, Rf=0.40. 1H-NMR (2 conformers 60:40, marked with * °, characteristic signals given): 8.72* (d, J=10 Hz, NH); 6.79*, 6.74° (2s, indole H-2); 6.35° (d, J=9.5 Hz, NH); 5.98* (d, J=6.5 Hz, NH); 5.32° (ddd, PrLeu alpha-H); 5.12°, 5.08* (2q, J=7 Hz, lactic acid Me); 4.50* (dd, MeLeu alpha-H); 4.06* (ddd, Leu alpha-H); 3.73 (s, indiole NMe); 3.44°, 3.19°, 3.15*, 2.93*, 2.53*, 2.35° (6s, NMe); 1.55*, 1.51° (2d, J=7 Hz, MeAla alpha-H), 1.39°, 1.24* (2d, J=7 Hz, lactic acid alpha-H); 0.57*, −0.09* (2d, J=6.5 Hz, Me), −0.32* (ddd, Leu beta-H).

Example 6

5-[8,11 -Diisobutyl-14-(1-methoxy-1H-indol-3-ylmethyl)-7,13,19,20-tetramethyl-5,17-bis-(2-methyl-hexyl)-3,6,9,12,15,18,21 -heptaoxo-1-oxa-4,7,10,13,16,19-hexaaza-cycloheneicos-2-yl]-pent-2-enoic acid methyl ester A solution of 185 mg of the compound of formula XV (see below) and 1.26 g of methoxy-carbonylmethylenetriphenylphosphorane in toluene is stirred at room termperature for 1 hour. Then the solvent is evaporated in vacuo, the residue chromatographed on a LH-20 gel-filtration column in methanol, the product containing fractions are evaporated in vacuo and further purified by chromatography on silica gel (eluent: gradient toluene/methanol=99.5/0.5 to 96/4) to yield the title product as a colorless solid foam. The product is lyophilized from benzene.

$^1$H-NMR (CDCl$_3$, characteristic signals, 3 conformers 53:41:6, marked with * °'): 8.67* (d, J=10 Hz, C$_9$AA NH); 7.87* (d, J=10 Hz, C$_9$AA NH); 7.80° (d, J=10 Hz, NH); 7.69° (d, J=10 Hz, NH); 7.45–7.35 (4d, MeMeOTrp H-4', H-7'); 7.23*, 7.22° (2m, MeMeOTrp H-6'); 7.4 (2m, MeMeOTrp H-5'); 7.06*, 7.00° (2s, MeMeOTrp H-2'); 6.88° (ddd, J=15 Hz, J=7 Hz, —CH=); 6.76* (ddd, J=15 Hz, J=7 Hz, —CH=); 6.240 (d, J=10 Hz, Leu NH); 6.04* (d, J=6 Hz, Leu NH); 5.820, 5.78* (2d, J=15 Hz, =CH—CO); 5.29° (ddd, MeAla a-H); 5.07–4.98 (m, a-H); 4.92 (dd, MeMeOTrp a-H); 4.86* (ddd, C$_9$AA a-H) 4.78* (dd, Leu a-H); 4.71 (m, a-H); 4.48* (dd, MeLeu a-H); 4.17* (ddd, Leu a-H); 4.06*, 4.03', 4.02° (3s, N-OMe); 3.75*, 3.74° (2s, COOMe); 3.43° (s, N-Me); 3.20*(s, MeAla NMe); 3.17°(s, N-Me); 2.92* (s, MeMeOTrp N-Me); 2.52* (s, MeLeu N-Me); 2.47° (s, N-Me); 1.51*, 1.480 (2d, J=7 Hz, MeAla β-Me); 1.04 (d, J=6.5 Hz, MeLeu Me); 0.98–0.84 (m); 0.63* (d, J=6.6 Hz, Leu Me); 0.56', 0.39' (2d); 0.06* (d, J=6.6 Hz, Leu Me); −0.11* (ddd, Leu β-CH).

Analogously as described in example 6 the ethyl ester is obtained.

The starting material of formula XV

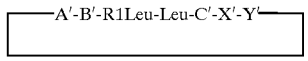

XV is known (WO 96/03430). In this formula the substituents have the following significances:

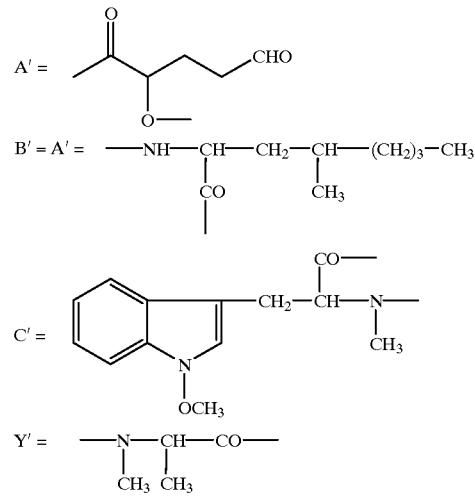

In the following examples 7–11, the same abbreviations are used with the exception that:

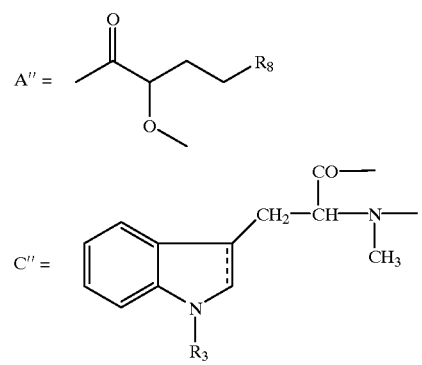

Example 7

Compound of formula IX (i.e. the compound of formula I, in which A=A", R$_8$=thiazol-2-yl, B=B', R$_1$=CH$_3$, C=C"', R$_3$=OCH$_3$, ==db, X=X',Y=Y')

A solution of 400 mg of the compound of formula I in which A=A", R$_8$=—CS NH$_2$, B=B' R$_1$=CH$_3$, C=C"', R$_3$=OCH$_3$, ==db, X=X', Y=Y') and 0.5 ml of choroacetal-dehyde hydrate in 8 ml of dry dimethylformamide is stirred with 0.5 g 4 Å molecular sieve and heated to 600 for 5 hours.

The mixture is then diluted with ethyl acetate, filtered and extracted with 0.1 N HCl. The organic phase is washed with brine, dried and evaporated in vacuo. The crude product is purified by chromatography on silica gel (eluent: gradient toluene/methanol=99.5/0.5 to 98/2) to yield the title compound as a solid foam.

Analogously as described in example 7 the following compounds of formula I are obtained (A=A", B=B' $R_1$=$CH_3$, C=C",$R_3$=$OCH_3$, ==db, X=X',Y=Y')

| Example | $R_8$ | |
|---|---|---|
| 8 | 2-methylthiazol-4-yl-phenyl | solid foam |
| 9 | 2-methyl-tetrahydrobenzothiazole | " |
| 10 | 2-methyl-4-methylthiazole | " |
| 11 | 2-methyl-4-tert-butylthiazole | " |

The starting material, i.e. the compound of formula I in which A=A', $R_8$=—CS $NH_2$, B=B' $R_1$=$CH_3$, C=C', $R_4$=$OCH_3$, ==db, X=X', Y=Y', is prepared in the following manner:

A solution of 1.1 g of the compound of formula XI (A is an α hydroxy substituted butyric acid residue γ substituted by —CN B=B' $R_1$=$CH_3$, C=C', $R_4$=$OCH_3$, ==db, X=X', Y=Y') and 1.8 g of diphenylphospinodithioic acid in 25 ml of isopropanol is heated to reflux for 7 hours. The reaction mixture is evaporated in vacuo, dissolved in ethyl acetate and extracted with sodium bicarbonate solution and brine. After evaporation of the organic layer the crude product is purified by chromatography on silica gel (eluent: gradient toluene/methanol=99.5/0.5 to 98/2) to yield the starting compound as colorless foam.

The compounds of Examples 4 to 11 have activities similar to that of the compound of formula VIII when measured in the VCAM-1 cell ELISA.

$^1$H-NMR Spectra ($CDCl_3$)

Ex.

7. 3 conformers 46:51:3, marked with *°': 8.70* (d, J=10 Hz, LeuPr NH); 7.89* (d, 10 Hz, NH); 7.83° (d, J=9 Hz, NH); 7.69, 7.66 (2d, J=3.3 Hz, thiazole H); 7.58 (d, J=10 Hz, NH); 7.53*, 7.47° (2dm, J=7 Hz, MeTrpOMe H-4'); 7.38*, 7.37° (2dm, J=8 Hz, MeTrpOMeH-7'); 7.22*, 7.20° (2tm, MeTrpOMe, H-6'); 7.17, 7.16 (2d, J=3.3 Hz, thiazole-H); 7.09 (s, MeTrpOMe H-2'); 7.03*, 7.00° (2dd, MeTrpOMe H-5'); 6.98° (s, MeTrpOMe H-2'); 6.18° (d, J=10 Hz, Leu NH); 6.03* (d, J=7 Hz, Leu NH); 5.80' (d, J=10 Hz, Leu NH); 5.30° (ddd, LeuPr a-H); 5.11* (dd, hydroxybutyric acid a-H); 5.05–4.98 (m, a-H); 4.94 (dd, MeTrpOMe a-H); 4.86° (ddd, LeuPr a-H); 4.73 (m, a-H); 4.49* (dd, MeLeu a-H); 4.23* (ddd, Leu a-H); 4.02, 4.00 (2s, N-OMe); 3.84° (m, a-H); 3.59–3.40 (m); 3.38 (q, J=7 Hz, MeAla a-H); 3.33 (s, N-Me); 3.2–2.85 (m); 3.21 (s, N-Me); 3.07 (s, N-Me); 2.93* (s, MeTrpOMe N-Me); 2.53* (s, MeLeu N-Me); 2.49 (s, N-Me); 2.43–2.28 (m); 2.18 (m); 1.98 (m); 1.81 (m); 1.7–1.1 (m); 1.48, 1.46 (2d, J=7 Hz, MeAla β-Me); 1.06* (d, J=6.5 Hz, MeLeu Me); 1.00–0.84 (m); 0.61* (d, J=6.6 Hz, Leu Me); 0.54' (d, J=6.6 Hz, Leu Me); 0.35' (d, J=6.6 Hz, Leu Me); 0.10* (d, J=6.6 Hz, Leu Me); −0.12* (ddd, Leu β-CH).

8. 3 conformers 47:48:5, marked with *°': 8.64* (d, J=10 Hz, LeuPr NH); 7.82 (2d, 10 Hz, NH); 7.63° (d, J=10 Hz, NH); 7.23, 7.17, 7.08, 6.97 (4t, arom. H); 7.32, 7.28 (2s, thiazole-H); 7.07 (s, MeTrpOMe H-2'); 6.81 (s, MeTrpOMe H-2'); 6.220 (d, J=10 Hz, Leu NH);

6.07* (d, J=7 Hz, Leu NH); 5.80' (d, J=10 Hz, Leu NH); 5.29° (ddd, LeuPr a-H); 5.20* (dd, MeTrpOMe a-H); 5.12° (dd, hydroxybutyric acid a-H); 5.030 (ddd, LeuPr a-H); 4.97* (ddd, LeuPr a-H); 4.85 (m, hydroxybutyric acid+ LeuPr a-H); 4.710 (ddd, Leu a-H); 4.52* (dd, MeLeu a-H); 4.21* (ddd, Leu a-H); 4.02, 3.90 (2s, N-OMe); 3.34 (s, N-Me); 3.22 (s, N-Me); 3.02 (s, N-Me); 2.93 (s, N-Me); 2.53 (s, N-Me); 2.48 (s, N-Me); 1.43, 1.42 (2d, J=7 Hz, MeAla β-Me); 1.06* (d, J=6.5 Hz, MeLeu Me); 0.62* (d, J=6.6 Hz, Leu Me); 0.10* (d, J=6.6 Hz, Leu Me); −0.04* (ddd, Leu β-CH).

9. 3conformers 42:52:6, marked with *°': 8.67* (d, J=10 Hz, LeuPr NH); 7.83, 7.80 (2d, 10 Hz, NH); 7.63° (d, J=10 Hz, NH); 7.55, 7.42, 7.39, 7.36 (4d, MeTrpOMe arom.); 7.22, 7.18, 7.05, 6.97 (4dd, MeTrpOMe H-5', H-6'); 7.06° (s, MeTrpOMe H-2'); 6.88* (s, MeTrpOMe H-2'); 6.220 (d, J=10 Hz, Leu NH); 6.02* (d, J=7 Hz, Leu NH); 5.77' (d, J=10 Hz, Leu NH); 5.30° (ddd, LeuPr a-H); 5.21* (dd, MeTrpOMe a-H); 5.0 (m, a-H); 4.85 (m, a-H); 4.65 (ddd, Leu a-H); 4.49* (dd, MeLeu a-H); 4.13* (ddd, Leu a-H); 4.03, 3.98 (2s, N-OMe); 3.70 (m); 3.55 (m); 3.45 (q, J=7 Hz, MeAla a-H); 3.37, 3.20, 3.11, 2.93, 2.52, 2.43 (6s, N-Me); 2.73 (m, tetrahydro-benzothiazol); 1.50, 1.48 (2d, J=7 Hz, MeAla β-Me); 1.04* (d, J=6.5 Hz, MeLeu Me); 0.58* (d, J=6.6 Hz, Leu Me); 0.50' (d, J=6.6 Hz, Leu Me); 0.30' (d, J=6.6 Hz, Leu Me); 0.03* (d, J=6.6 Hz, Leu Me); −0.22* (ddd, Leu β-CH).

10. 3 conformers 44:51:5, marked with *°': 8.66* (d, J=10 Hz, LeuPr NH); 7.83, 7.81 (2d, 10 Hz, NH); 7.630 (d, J=10 Hz, NH); 7.57*, 7.43°, 7.38*, 7.36° (4d, J=8 Hz, indole-H); 7.21*, 7.18°, 7.05, 6.97 (4t, indole-H); 7.06* (s, MeTrpOMe H-2'); 6.88* (s, MeTrpOMe H-2'); 6.70°, 6.69* (2q, J=1 Hz, thiazole-H); 6.23° (d, J=10 Hz, Leu NH); 6.05* (d, J=7 Hz, Leu NH); 5.80' (d, J=10 Hz, Leu NH); 5.29° (ddd, LeuPr a-H); 5.11° (dd, hydroxybutyric acid a-H); 5.01 (m); 4.97 (dd, a-H); 4.85 (m, 2×a-H); 4.69° (ddd, Leu a-H); 4.57' (dd, a-H); 4.48* (dd, MeLeu a-H); 4.16* (ddd, Leu a-H); 4.03, 3.98 (2s, N-OMe); 3.43 (q, J=7 Hz, MeAla a-H); 3.37, 3.20, 3.10, 2.92, 2.52, 2.46 (6s, N-Me); 2.40, 2.39 (2d, J=1 Hz, Me-thiazole); 1.48, 1.47 (2d, J=7 Hz, MeAla β-Me); 1.05* (d, J=6.5 Hz, MeLeu d-Me); 0.60* (d, J=6.6 Hz, Leu d-Me); 0.52', 0.33' (2d, J=6.5 Hz Leu d-Me); 0.05* (d, J=6.6 Hz, Leu d-Me); −0.14* (ddd, Leu β-CH).

11. 3 conformers 47:50:3, marked with *°': 8.69* (d, J=10 Hz, LeuPr NH); 7.79, 7.78 (2d, 10 Hz, NH); 7.650 (d, J=10 Hz, NH); 7.51*, 7.41°, 7.39*, 7.38° (4d, J=8 Hz, indole-H); 7.23*, 7.20°, 7.07, 7.00 (4t, indole-H); 7.04* (s, MeTipOMe H-2'); 6.85° (s, MeTrpOMe H-2'); 6.71°* (s, thiazole-H); 6.25° (d, J=10 Hz, Leu NH); 6.04* (d, J=7 Hz, Leu NH); 5.80' (d, J=10 Hz, Leu NH); 5.30° (ddd, LeuPr a-H); 5.10° (dd, hydroxybutyric acid a-H); 5.02 (m); 4.97 (dd, a-H); 4.85 (m, 2×a-H); 4.72° (ddd, Leu a-H); 4.60' (dd, a-H); 4.50* (dd, MeLeu a-H); 4.17* (ddd, Leu a-H); 4.04,4.00 (2s, N-OMe); 3.48 (q, J=7 Hz, MeAla a-H); 3.41, 3.21, 3.17, 2.92, 2.53, 2.47 (6s, N-Me); 0.97, 0.96 (2s, t-Bu-thiazole); 1.50, 1.49 (2d, J=7 Hz, MeAla β-Me); 1.06* (d, J=6.5 Hz, MeLeu d-Me); 0.62* (d, J=6.6 Hz, Leu d-Me); 0.53', 0.35' (2d, J=6.5 Hz Leu d-Me); 0.07* (d, J=6.6 Hz, Leu d-Me); −0.08* (ddd, Leu β-CH).

A) 3 conformers 44:30:26, marked with *°': 8.85 (d, CSNH$_2$); 8.60 (d, LeuPr NH); 8.17 (d, CSNH$_2$); 8.03, 8.00 (2d, NH); 7.88 (m, CSNH$_2$); 7.6–7.1 (arom.); 6.28* (d, 10 Hz, Leu NH); 6.07° (d, 7 Hz, Leu NH); 5.87' (d, 9 Hz, Leu NH); 5.26* (ddd, LeuPr a-H), 5.22 (dd, hydroxy acid a-H); 5.15–4.95, 5.08* (dd, hydroxy acid a-H); 4.83° (ddd, LeuPr a-H); 4.50* (ddd, Leu a-H); 4.37* (dd, MeTrpOMe a-H); 4.25° (ddd, Leu a-H); 4.09, 4.05, 4.03* (3s, OMe); 3.89 (m, a-H); 3.65*, 3.63', 3.52° (3q, 7 Hz, MeAla a-H); 3.57 (m), 3.17, 3.16, 3.15, 3.22, 3.20, 3.05, 2.92, 2.55, 2.53 (9s, N-Me); 1.8–1.1; 1.05 (d, 7 Hz); 0.99–0.82, 0.60°, 0.55', 0.23', 0.17° (4d, 7 Hz, Leu d-Me); −0.15°, −0.17' (ddd, Leu b-CH). PKF 285–916 (thiazole).

Biological Activity

The activities of the compounds of the invention are tested in assays for cytotoxicity and inhibition of ICAM-1, VCAM-1 and E-selectin expression, cell proliferation, as well as for inhibition of TNF release and a corresponding assay for cytotoxicity.

The assays are carried out as follows:

HaCaT cells, a spontaneously-transformed, non-tumorigenic human keratinocyte cell line with highly preserved phenotypic differentiation characteristics of normal keratinocytes (Boukamp et al., 1988 J. Cell Biol. 106, 761–771), are used both for the cell proliferation assay and the ICAM-1 cell Elisa.

A. ICAM-1 CELL-ELISA ASSAY

I. Keratinocyte ICAM-1 Cell Elisa

The ICAM-1 cell Elisa used to determine inhibition of ICAM-1 expression is substantially as described by Winiski and Foster (1992, J. Invest. Dermatol., 99, 48–52). HaCaT cells are seeded in 96 well microtiter plates ($2 \times 10^4$ cells/well in culture medium: DMEM with 5% FCS, 100 U/ml Penicillin, 100 mg/ml Streptomycin, 2 mM Glutamine, 1 mM Na Pyruvate), grown to confluency, and then incubated in fresh test medium (as for culture medium but with 0.5% FCS instead of 5%) with or without IFN-γ/TNF-α stimulation medium (test medium+1000 U/ml IFN-γ/3 ng/ml TNF-α) both in the presence and absence of the test compound for ca. 24 hrs. The medium is then washed away and the cell monolayers are fixed with 1% parafomraldehyde. The monolayers are incubated with saturating amounts of primary (mouse anti-ICAM-1 monoclonal) and secondary (goat anti-mouse peroxidase conjugated) antibodies. The subsequent peroxidase reaction uses 3-amino-9-ethylcarbazole (AEC) as substrate and generates an insoluble, colored product, which is easily measured in a standard microtiter plate reader.

II. Measure of Cytotoxicity

After the AEC reaction to detect ICAM-1 is completed, the HaCaT monolayers, are rinsed with PBS (200 mL), the PBS is poured off from the plates which are then patted dry on top of a paper towel to remove excess liquid. The bottom surfaces of the microtitre plates are gently wiped with a moist facial tissue and then again with a dry facial tissue and absorbance read at 492 nm. Before the monolayers can dry out, 0.1 ml of 0.1% crystal violet solution in PBS (passed first through a 0.2 mm filter) is added to each well. The plates are then incubated at room temperature for 10 minutes, washed thoroughly 5× with PBS, excess fluid removed as described above and their absorbance read again at 492 nm before the monolayers are able to dry out. Subtraction of optical densities before and after staining gives values due to crystal violet staining and is hence related to the amounts of cell monolayer present in the wells. These values are used to correct the AEC values.

B. Endothelial cell VCAM-1, ICAM-1 and E-selectin Cell-Elisa Assay

The assay is based on a 96-well cell Elisa method using the human microvascular endothelial cell line HMEC-1 and human umbilical vein endothelial cells (HUVEC). Cells are pretreated for four hours with the test compound, stimulated for the next 6–16 hours with TNFα, then parafomaldehyde-fixed for subsequent evaluation of VCAM-1, ICAM-1 or E-selectin expression by an indirect immunoperoxidase staining technique. Cytotoxic effects are determined by counting the relative number of cells (Giemsa nuclear stain) after exposure to the test substances, in comparison to the control wells (solvent and media only). Compounds are scored positive if they exhibit >50% VCAM-1, ICAM-1 or E-selectin inhibition with <25% cell loss.

Methodology

I. Cell line: The VCAM-1 and ICAM-1 assay utilizes an immortalized (SV-40 virus large T antigen) human microvascular endothelial cell line (HMEC-1; Ades et al., J. Invest. Dermatol. 99: 683–690, 1992). HMEC-1 cells constitutively express low levels of ICAM-1 which are upregulated by inflammatory mediators. However, they only express VCAM-1 following cytokine stimulation. Dose-response and time-course experiments were performed to determine the optimal conditions for inducing VCAM-1 and ICAM-1 expression.

II. Growth conditions: HMEC-1 cells are grown in T-75 flasks (Nunc) under standard conditions (37° C., 5% C02) with $1.5 \times 10^6$ cells/ml culture medium (CM=Endothelial Cell Basal Medium [EBM; Clonetics] supplemented with 10% FCS, 10 ng/ml human EGF (Boehringer), 1 mg/ml hydrocortisone (Sigma #0888), 2.2 g/l NaHCO$_3$, 15 mM Hepes, 0.11 g/l sodium pyruvate, 4 mM glutamine, 100 U/ml penicillin and 100 mg/ml streptomycin). After mild trypsinization (0.25% trypsin+0.1% EDTA for 8 min) and resuspension, the cells are reseeded every 2–3 days at a 1:3 splitting ratio.

III. VCAM-1 and ICAM-1 Cell-Elisa 96 well flat-bottom microtiter plates are precoated with bovine fibronectin (FN; Sigma #F1141) and then seeded with $2 \times 10^4$ cells/well in 200 ml of EBM growth medium and incubated overnight. The following day the culture medium (CM) is initially replaced with 2.00 ml/well of EBM assay medium (CM supplemented with 5% FCS instead of 10%) and subsequently replaced with 180 ml of medium containing either (1) appropriate concentrations of the test compound, (2) corresponding concentrations of solvent/methanol-extracted medium, or (3) EBM assay medium alone and incubated for 4 hr at 37° C. Each 96-well assay is performed with duplicate wells. The cells are then stimulated by adding 20 ml of concentrated cytokine solution (2000 U/ml TNFa) and incubated for 16 hr at 37° C.

The cell monolayer is then washed with 1% parafornaldehyde in EBM medium, fixed in 2% parafomaldehyde for 15 min at room temperature (RT) and rinsed several times with PBS. The PBS is removed from the cells, and the monolayer is incubated for 30 min in PBS containing 10% normal goat serum (NGS). The NGS solution is replaced with 100 ml/well of the anti-VCAM-1 or ICAM-1 monoclonal antibody and incubated overnight at 4° C. The mAb solution is then removed and the cells rinsed several times with PBS, followed by incubation with PBS containing 10% NGS for 30–60 min at RT. The NGS solution is removed and 100 ml of horseradish peroxidase-conjugated goat F(Ab')$_2$ anti-mouse IgG antibody (Tago; 1:500 dilution in PBS containing 5% NGS) is added and the plates incubated for 1 hr at RT. The secondary antibody is then removed and the cells rinsed in PBS, which is then replaced with 150 mn/well of a freshly-prepared and filtered AEC solution (3-amino-9ethyl-carbazole; Sigma) and the plates incubated for 45–60 min at RT. The peroxidase substrate is removed and the cells rinsed in PBS. AEC absorbance values are read on a microtiter plate reader at 550 nm and corrected for "blank" or reference values at 690 nm.

IV. E-selectin assay: The E-selectin assay is performed using freshly isolated HUVEC, essentially as described for the VCAM-1 or ICAM-1 assay except for a shorter TNFa-stimulation (6–8 hours).

V. Measure of Cytotoxicity (Cell loss based on nuclear stain):

The endothelial cells are destained by replacing the PBS with 95% ethanol for 20 min (two 10 min changes) with control by microscopic evaluation. The cells are then rinsed in distilled water (Aquadest) and the monolayer covered with a 33% Giemsa solution in Aquadest for 5 min at RT. The wells are then washed with Aquadest and air dry for at least 15 min. Microscopic evaluation is used to check that only the nuclei are stained, with essentailly no cytoplasmic staining. Giemsa absorbance values are read on a microtiter plate reader at 550 nm and corrected for "blank" values (rows without cells) at 690 nm.

VI. Data Evaluation: The AEC values for constitutive VCAM-1 or E-selectin expression (unstimulated control wells) are essentially equal to those of an isotype-matched control mAb and represent the background stain. In every 96-well plate, the mean constitutive value is subtracted from the mean AEC value for each cytokine-stimulated group (EBM and solvent controls, as well as test substance), resulting in a number which represents upregulated ICAM-1 and inducible VCAM-1 or E-selectin Cell adhesion molecule (CAM) expression (referred to as AEC-CAM). Each AEC-CAM value is then divided by the corresponding mean Giemsa value, resulting in a number which estimates relative levels of CAM expression for a given cell density, based on the number of nuclei (referred to as AEC: Giemsa ratio).

AEC(stimulated)−AEC(unstimulated)=AEC−CAM

AEC−CAM/Giemsa=AEC:Giemsa ratio

Therefore "actual" CAM IC$_{50}$ values are determined by comparing the AEC:Giemsa values for a test substance with those of the stimulated control (EBM, solvent). These values are then analyzed relative to the IC$_{50}$ values for Giemsa alone. Strict criteria determine whether the CAM inhibition versus cytotoxicity (Giemsa) profile indicates a "real" hit which should be pursued.

C. HaCaT cell PROLIFERATION ASSAY

HaCaT cells are cultivated in DMEM (Gibco #074–02100) supplemented with 2.2 g/l NaHCO$_3$, 0.11 g/l sodium pyruvate, 15 mM Hepes, 5% fetal calf serum (FCS), penicillin (100 U/ml), streptomycin (100 mg/ml), and glutamine (to increase the final concentration by 4 mM). For the proliferation assay, cells are detached by trypsinization, suspended in fresh medium, and seeded into 96-well microtiter plates at a final density of 4000 cells/0.2 ml/well. After 24 hours (day 0) the medium is replaced with fresh medium containing graded concentrations of test compound. After 3 days of incubation at 37° C./5%CO$_2$, the extent of cellular proliferation in comparison to solvent controls is measured by a colorimetric assay that measures relative cell mass using the dye sulforhodamine B (Skehan et al, 1990, J. Natl. Cancer Inst. 82, 1107–1112). The "starting cell number" is determined by measuring the relative cell mass on day 0. The results are expressed as % Inhibition=100-% control absorbance (where solvent control=100%) and represent the average±standard deviation of three measurements. A dose-response curve is plotted semi-logarithmically and the concentration required for half-maximal inhibition (IC$_{50}$) is determined by linear interpolation. Maximal inhibition without net loss of cells is represented by the "starting cell number" and is usually between 90–98%.

D. Inhibition of TNF release

I.

Mononuclear cells are prepared from the peripheral blood of healthy volunteers using ficoll-hypaque density separation according to the method of Hansell et al. (J. Imm. Methods (1991) 145: 105.) and used at a concentration of 10$^5$ cells/well in RPMI 1640 plus 10% FCS. Cells are incubated with serial dilutions of the test compounds for 30 minutes at 37° C. prior to the addition of IFNγ (100 U/ml) and LPS (5 mg/ ml) and subsequently further incubated for three hours. Incubation is terminated by centrifugation at 1400 RPM for 10 min. TNFα in the supernatant is measured using a commercial ELISA (Innotest hTNFα, available from Innogenetics N.V., Zwijnaarde, Belgium). The compounds are tested at concentrations of from 0 to 10 mM. Exemplified compounds of formula I, especially preferred compounds of formula Ip, Ip', Ip'', VII, IX and X, suppress TNF release in this assay with an IC$_{50}$ of from about 5 up to about nM.

II. Cytotoxicity

Cytotoxicity is determined on THP1 cells (5×10$^4$/well) which are incubated in the presence of IFNγ(100 U/ml) and LPS (5 mg/ ml) and presence and absence of test compound for 24 hours at 37° C. Percentages of living and dead cells are assessed by a colorimetric readout (MTT), which measures mitochondrial dehydrogenase enzymes in living cells, as described in Mosman, J. Imm. Methods (1983) 65:55. Preferred compounds of the invention typically have comparitively low cytotoxicity when measured in this assay, e.g. an IC$_{50}$ of from about 100 up to about 1000 nM.

We claim:

1. A cyclopeptide of formula I in free, salt or ester form:

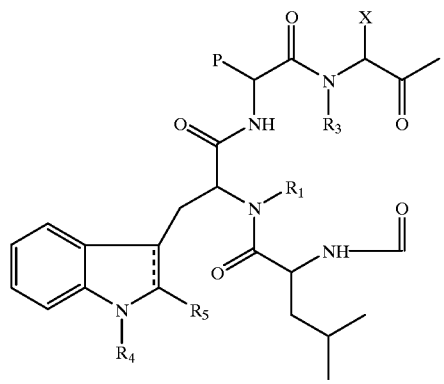

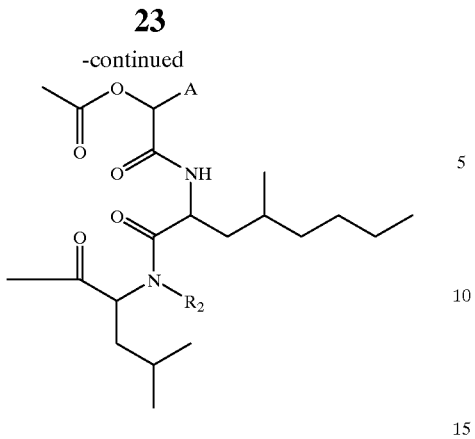

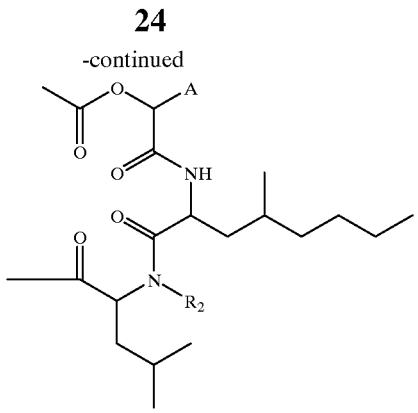

Wherein A is substituted by:
H, methyl, ethyl, propyl, or vinyl, optionally substituted by
Halogen, alkoxy, optionally protected hydroxy or amino, CSNH2, COOR2, vinyl, —C≡CH or thiazole, wherein R2 is H or lower alkyl,
optionally substituted by
alkyl, halogen, cycloalkyl, optionally substituted thiazole, COOR2 or —C≡CH,
wherein R2 is as defined above;
R1, R2, R3 are H or methyl;
R4 is H, alkoxy, alkyl, or benzyl;
R5 is H or halogen;
= represents a single or double bond;
P is C2 to C14 alkyl;
X is C2 to C10 alkyl.

2. A compound of formula I

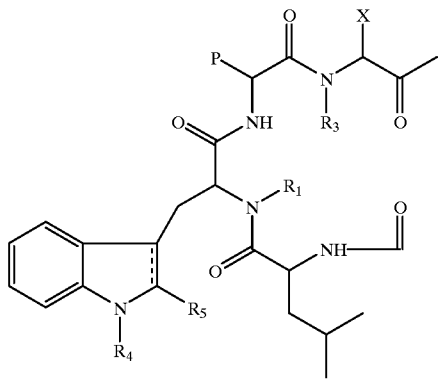

Wherein A is H, ethyl, or methyl;

R1, R2, R3 are hydrogen or methyl;

R4 is Cl to C4 alkoxy;

R5 is H or halogen;

= represents a single or double bond;

P is C2 to C14 alkyl;

X is C2 to ClO alkyl.

3. A compound of claim 1 wherein A is:

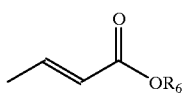

wherein R6 represents a lower alkyl group.

4. A compound of claim 1, wherein A is:

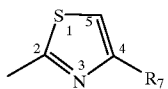

Wherein R7 represents hydrogen, lower alkyl, phenyl or forms a carbocyclic ring together with position 5 of the thiazolyl ring.

5. A cyclopeptolide of formula VII, IX or X in free or salt form

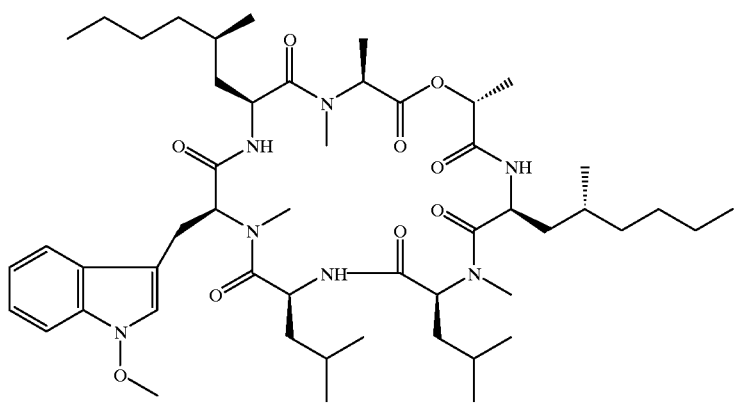
VIII
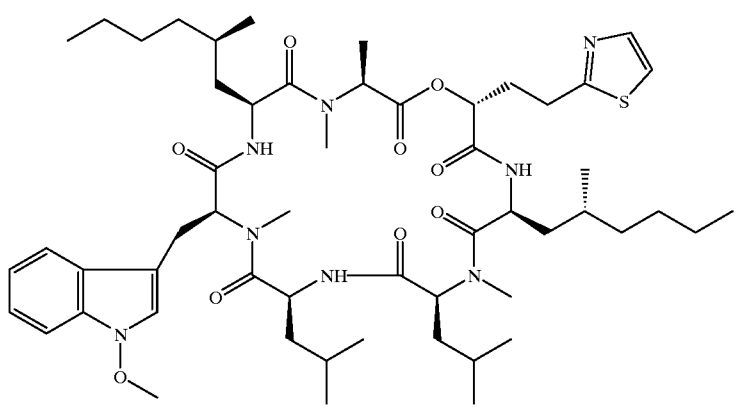
IX
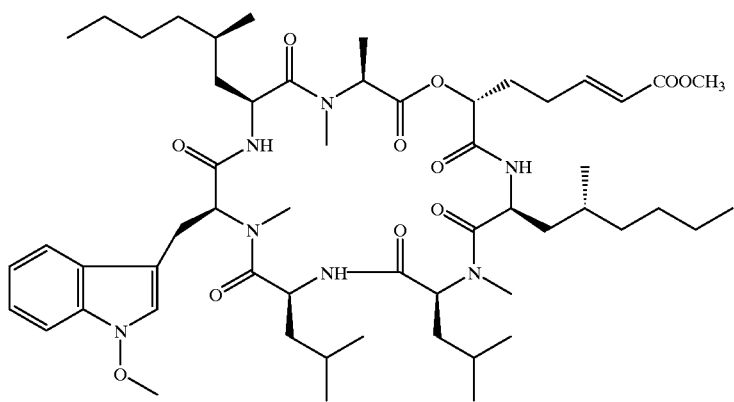
X
* * * * *

UNITED STATES PATENT AND TRADEMARK OFFICE
CERTIFICATE OF CORRECTION

PATENT NO. : 6,011,136
DATED : January 4, 2000
INVENTOR(S) : DREYFUSS ET AL.

It is certified that error appears in the above-indentified patent and that said Letters Patent is hereby corrected as shown below:

On the title page, section [22]. should read:

-- [22] PCT filed:   November 20, 1996 --

Claim 1, in column 23, last line of said claim should read:
-- X is C2 to C10 alkyl. --.

Signed and Sealed this

Twenty-seventh Day of March, 2001

Attest:

NICHOLAS P. GODICI

Attesting Officer

Acting Director of the United States Patent and Trademark Office